US00PP30647P3

(12) United States Plant Patent
Palmer et al.

(10) Patent No.: US PP30,647 P3
(45) Date of Patent: Jul. 2, 2019

(54) ***DAHLIA* PLANT NAMED 'G14402DAHL'**

(50) Latin Name: *Dahlia variabilis*
Varietal Denomination: G14402DAHL

(71) Applicants: Irene E. Palmer, Mills River, NC (US); Michael S. Uchneat, Bellefonte, PA (US)

(72) Inventors: Irene E. Palmer, Mills River, NC (US); Michael S. Uchneat, Bellefonte, PA (US)

(73) Assignee: Garden Genetics LLC, Bellefonte, PA (US)

( * ) Notice: Subject to any disclaimer, the term of this patent is extended or adjusted under 35 U.S.C. 154(b) by 62 days.

(21) Appl. No.: 15/732,087

(22) Filed: Sep. 14, 2017

(65) Prior Publication Data

US 2019/0082576 P1 Mar. 14, 2019

(51) Int. Cl.
*A01H 5/02* (2018.01)
*A01H 6/14* (2018.01)

(52) U.S. Cl.
USPC ..... Plt./321
CPC ..... *A01H 6/144* (2018.05)

(58) Field of Classification Search
USPC ..... Plt./321
See application file for complete search history.

*Primary Examiner* — Anne Marie Grunberg
(74) *Attorney, Agent, or Firm* — C. A. Whealy

(57) ABSTRACT

A new and distinct cultivar of *Dahlia* plant named 'G14402DAHL', characterized by its upright and mounding plant habit; vigorous growth habit; freely branching habit; dark green-colored leaves; early and freely flowering habit; and large semi-double type inflorescences with greyed purple-colored ray florets.

1 Drawing Sheet

Botanical designation: *Dahlia variabilis*.
Cultivar denomination: 'G14402DAHL'.

BACKGROUND OF THE INVENTION

The present invention relates to a new and distinct cultivar of *Dahlia* plant, botanically known as *Dahlia variabilis* and hereinafter referred to by the name 'G14402DAHL'.

The new *Dahlia* plant is a product of a planned breeding program conducted by the Inventor in Bellefonte, Pa. The objective of the breeding program is to create new vigorous *Dahlia* plants that have dark-colored leaves, large attractive inflorescences and reduced sensitivity to Powdery Mildew.

The new *Dahlia* plant originated from a cross-pollination in Bellefonte, Pa. in July, 2013 of a proprietary selection of *Dahlia variabilis* identified as code number 3180-5M-2M-2, not patented, as the female, or seed, parent with a proprietary selection of *Dahlia variabilis* identified as code number 3198-1-1, as the male, or pollen, parent. The new *Dahlia* plant was discovered and selected by the Inventors as a single flowering plant from within the progeny of the stated cross-pollination in a controlled greenhouse environment in Bellefonte, Pa. on Mar. 14, 2014.

Asexual reproduction of the new *Dahlia* plant by vegetative terminal cuttings in a controlled greenhouse environment in Bellefonte, Pa. since Oct. 13, 2014 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'G14402DAHL'. These characteristics in combination distinguish 'G14402DAHL' as a new and distinct *Dahlia* plant:

1. Upright and mounding plant habit.
2. Vigorous growth habit.
3. Freely branching habit.
4. Dark green-colored leaves.
5. Early and freely flowering habit.
6. Large semi-double type inflorescences with greyed purple-colored ray florets.

Compared to plants of the female parent selection, plants of the new *Dahlia* differ primarily in the following characteristics:

1. Plants of the new *Dahlia* are more mounding than and not as upright as plants of the female parent selection.
2. Plants of the new *Dahlia* have semi-double type inflorescences whereas plants of the female parent selection have single type inflorescences.
3. Plants of the new *Dahlia* and the female parent selection differ in ray floret color as plants of the female parent selection have pink-colored ray florets.

Compared to plants of the male parent selection, plants of the new *Dahlia* differ primarily in the following characteristics:

1. Plants of the new *Dahlia* are more vigorous than and not as compact as plants of the male parent selection.
2. Plants of the new *Dahlia* have semi-double type inflorescences whereas plants of the male parent selection have single type inflorescences.

3. Plants of the new *Dahlia* and the male parent selection differ in ray floret color as plants of the male parent selection have lavender-colored ray florets.

Plants of the new *Dahlia* can be compared to plants of *Dahlia* 'Mystic Wonder', disclosed in U.S. Plant Pat. No. 24,397. In side-by-side comparisons, plants of the new *Dahlia* differ primarily from plants of 'Mystic Wonder' in the following characteristics:

1. Plants of the new *Dahlia* are more mounding than and not as upright as plants of 'Mystic Wonder'.
2. Plants of the new *Dahlia* have semi-double type inflorescences whereas plants of 'Mystic Wonder' have single type inflorescences.
3. Plants of the new *Dahlia* and 'Mystic Wonder' differ in ray floret color as plants of 'Mystic Wonder' have red-colored ray florets.

Plants of the new *Dahlia* can also be compared to plants of *Dahlia* 'G13525', disclosed in U.S. Plant Pat. No. 28,223. In side-by-side comparisons, plants of the new *Dahlia* differ primarily from plants of 'G13525' in ray floret color as plants of 'G13525' have greyed red-colored ray florets.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph at the bottom of the sheet is a side perspective view of a typical flowering plant of 'G14402DAHL' grown in a container.

The photograph at the top of the sheet is a close-up view of a typical flowering plant of 'G14402DAHL'.

DETAILED BOTANICAL DESCRIPTION

The aforementioned photographs and following observations and measurements describe plants grown during the spring in 11.5-cm containers in an acrylic-covered greenhouse in Carleton, Mich. and under cultural practices typical of commercial potted *Dahlia* production. During the production of the plants, day and night temperatures ranged from 18° C. to 27° C. Plants were eleven weeks old when the photographs and description were taken. In the following description, color references are made to The Royal Horticultural Society Colour Chart, 2007 Edition, except where general terms of ordinary dictionary significance are used.

Botanical classification: *Dahlia variabilis* 'G14402DAHL'.

Parentage:

*Female, or seed, parent*.—Proprietary selection of *Dahlia variabilis* identified as code number 3180-5M-2M-2, not patented.

*Male, or pollen, parent*.—Proprietary selection of *Dahlia variabilis* identified as code number 3198-1-1, not patented.

Propagation:

*Type*.—By vegetative terminal cuttings.

*Time to initiate roots, summer*.—About 7 to 10 days at ambient temperatures about 22° C. to 27° C.

*Time to initiate roots, winter*.—About 10 to 14 days at ambient temperatures about 18° C. to 23° C.

*Time to produce a rooted plant, summer*.—About three to four weeks at ambient temperatures about 22° C. to 27° C.

*Time to produce a rooted plant, winter*.—About four weeks at temperatures about 18° C. to 23° C.

*Root description*.—Medium in thickness, fleshy and fibrous; close to white to creamy white in color, actual color of the roots is dependent on substrate composition, water quality, fertilizers, substrate temperature and age of roots; tuber development has not been observed on plants of the new *Dahlia* to date.

*Rooting habit*.—Freely branching; medium density.

Plant description:

*Plant and growth habit*.—Upright and mounded plant form; broad inverted triangle; freely branching habit with about seven primary lateral branches each with about six to seven secondary lateral branches developing per plant; inflorescences held mostly above and beyond the foliar plane on moderately strong peduncles; vigorous growth habit and moderate growth rate.

*Plant height, soil level to top of foliar plane*.—About 36 cm.

*Plant height, soil level to top of floral plane*.—About 41 cm.

*Plant diameter or spread*.—About 47 cm.

*Lateral branches*.—Length: About 35 cm. Diameter: About 8 mm. Internode length: About 5 cm. Strength: Strong. Aspect: Primary laterals, mostly erect; secondary laterals, about 15° to 45° from vertical. Texture: Smooth, glabrous. Luster: Somewhat glossy. Color: Developing, close to N199B; color becoming closer to 200A with subsequent development.

Leaf description:

*Arrangement*.—Opposite; simple.

*Length*.—About 14.8 cm.

*Width*.—About 17.5 cm.

*Shape*.—Pinnatifid; deeply incised with five to seven lobes with parallel sinuses.

*Lobe length*.—About 7 cm.

*Lobe width*.—About 3.5 cm.

*Apex*.—Acute.

*Base*.—Attenuate, equilateral.

*Margin*.—Crenate.

*Venation pattern*.—Pinnate.

*Texture, upper and lower surfaces*.—Smooth and mostly glabrous with minute hairs along veins.

*Luster, upper and lower surfaces*.—Matte.

*Color*.—Developing leaves, upper surface: Close to N137A. Developing leaves, lower surface: Close to 148A. Fully expanded leaves, upper surface: Darker than N137A; venation, close to 200B. Fully expanded leaves, lower surface: Close to 148A; venation, close to N199A.

*Petioles*.—Length: About 6 cm. Diameter: About 4 mm. Strength: Strong. Texture, upper and lower surfaces: Smooth, glabrous. Luster, upper and lower surfaces: Matte. Color, upper surface: Close to 200A. Color, lower surface: Close to N199A.

Inflorescence description:

*Appearance and arrangement*.—Semi-double inflorescence form with ray florets forming acropetally on a receptacle; inflorescences positioned above the foliar plane on moderately strong peduncles; inflorescences mostly nodding; freely flowering habit with about 60 inflorescences developing per plant.

*Fragrance*.—Slightly fragrant; sour.

*Time to flower*.—Early flowering habit, plants begin flowering about six weeks after planting; plants flower continuously from spring until frost in Michigan.

*Post-production longevity*.—Inflorescences maintain good substance for about five to six days on the plant; ray florets not persistent and disc florets persistent.

*Inflorescence buds*.—Height: About 2.2 cm. Diameter: About 2.2 cm. Shape: Flattened sphere. Texture and luster: Smooth, glabrous; somewhat glossy. Color: Phyllaries, close to N199C; ray florets, close to N79A.

*Inflorescence size*.—Diameter: About 8 cm. Depth (height): About 2.6 cm. Disc diameter: About 2 cm.

*Receptacles*.—Height: About 1 cm. Diameter: About 5 cm. Shape: Rounded, bowl-shape. Color: Close to 200C to 200D tinted with close to 146A.

*Ray florets*.—Quantity per inflorescence: About 28 arranged in about two whorls. Length: About 3.4 cm. Width: About 2.2 cm. Shape: Obovate. Apex: Rounded to slightly emarginate. Base: Attenuate, fused at base. Margin: Entire; slightly undulate. Aspect: Initially upright to roughly perpendicular to the peduncle with apices slightly reflexed. Texture, upper and lower surfaces: Longitudinally ridged, glabrous; velvety. Luster, upper and lower surfaces: Matte. Color: When opening, upper surface: Close to N79A. When opening, lower surface: Close to N79B. Fully opened, upper surface: Close to 187A; venation, close to 187A; color does not change with development. Fully opened, lower surface: Close to 187B to 187C; venation, close to 187B; color does not change with development.

*Disc florets*.—Quantity per inflorescence: About 106 arranged in about ten whorls. Length: About 1.7 cm. Diameter: About 2 mm. Shape: Tubular, elongated; apices acute. Texture: Smooth, glabrous. Luster: Moderately glossy to glossy. Color, when opening: Darker than 187A to 187A. Color, fully opened: Close to 187A.

*Phyllaries*.—Quantity per inflorescence: One inner whorl with about 14 phyllaries that are membraneous and closely appressed to the receptacle and one outer whorl with about six phyllaries that are bract-like and reflex downwardly. Inner whorls: Length: About 2 cm. Width: About 9 mm. Shape: Elliptical. Apex: Acute. Base: Truncate. Margin: Entire. Texture, upper and lower surfaces: Smooth, glabrous. Luster, upper and lower surfaces: Glossy. Color, upper surface: Close to N199D. Color, lower surface: Close to N199C. Outer whorls: Length: About 1.5 cm. Width: About 6 mm. Shape: Elliptical. Apex: Acute. Base: Truncate. Margin: Entire. Texture, upper and lower surfaces: Smooth, glabrous. Luster, upper and lower surfaces: Slightly glossy. Color, upper surface: Darker than 189A. Color, lower surface: Close to N137A.

*Peduncles*.—Length, terminal peduncles: About 6.5 cm. Diameter, terminal peduncles: About 2 mm. Length, axillary peduncles: About 5.9 cm. Diameter, axillary peduncles: About 2 mm. Aspect, terminal peduncles: Mostly erect to bent with the weight of the inflorescences. Aspect, axillary peduncles: About 45° to 55° from lateral branch axis. Strength: Moderately strong. Texture: Smooth, glabrous. Luster: Somewhat glossy. Color: Close to 187A.

*Reproductive organs*.—Present on disc florets only. Androecium: Quantity per floret: Five. Filament length: About 8 mm. Filament color: Close to 151D. Anther shape: Lanceolate. Anther size: About 5 mm by 1 mm. Anther color: Close to 187B. Pollen amount: Moderate. Pollen color: Close to 17C. Gynoecium, ray florets: Quantity per floret: One. Pistil length: About 7 mm. Style length: About 4 mm. Style color: Close to N163D. Stigma diameter: About 2 mm. Stigma shape: Bi-parted. Stigma color: Close to N163D. Ovary color: Close to 157A. Gynoecium, disc florets: Quantity per floret: One. Pistil length: About 1.5 cm. Style length: About 8 mm. Style color: Close to N163D. Stigma diameter: About 2 mm. Stigma shape: Bi-parted. Stigma color: Close to N163D. Ovary color: Close to 157A. Seeds and fruits: Seed and fruit development have not been observed on plants of the new *Dahlia* to date.

Disease & pest resistance: Plants of the new *Dahlia* have not been observed to be resistant to pathogens and pests common to *Dahlia* plants to date.

Temperature tolerance: Plants of the new *Dahlia* have been observed to tolerate low temperatures about 1.7° C. and to be suitable for USDA Hardiness Zones 8 to 11.

It is claimed:

1. A new and distinct *Dahlia* plant named 'G14402DAHL' as illustrated and described.

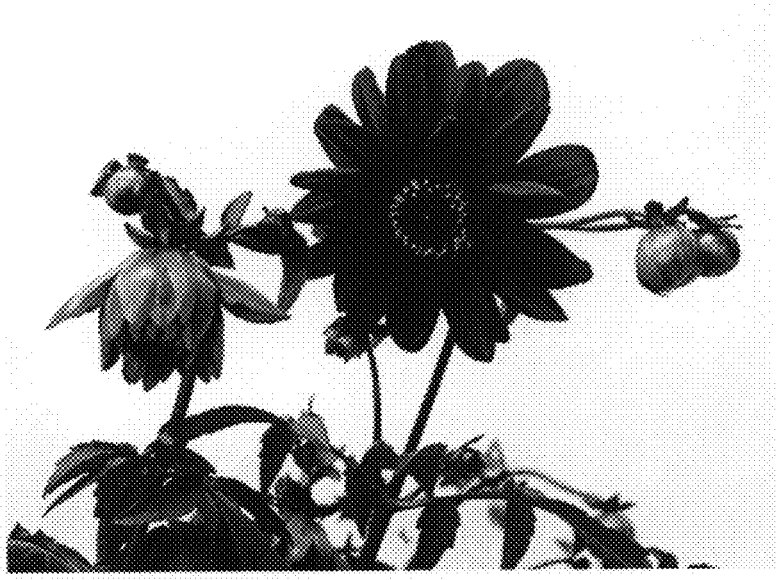
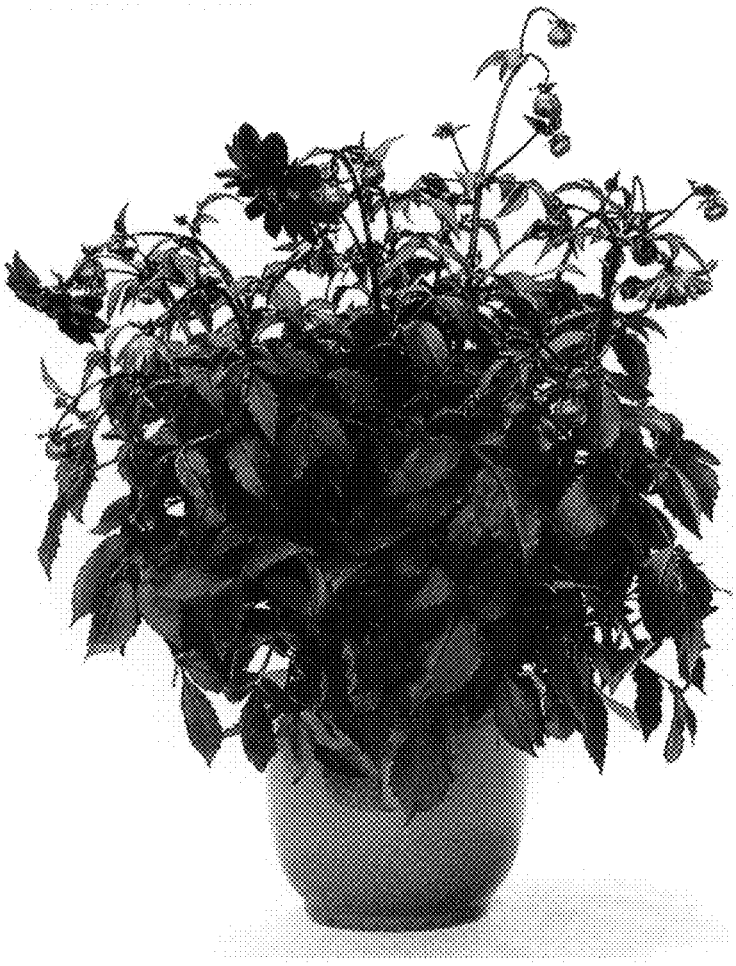

* * * * *